(12) United States Patent
Teng et al.

(10) Patent No.: US 6,943,186 B2
(45) Date of Patent: Sep. 13, 2005

(54) METHODS OF TREATING SEPSIS

(75) Inventors: Che-Ming Teng, Taipei (TW); Shiow-Lin Pan, Taipei (TW); Jih-Hwa Guh, Taipei (TW); Sheng-Chu Kuo, Taichung (TW); Fang-Yu Lee, Tachia Taichung (TW)

(73) Assignee: Yung Shin Pharmaceutical Ind. Co., Ltd., Taipei (TW)

( * ) Notice: Subject to any disclaimer, the term of this patent is extended or adjusted under 35 U.S.C. 154(b) by 216 days.

(21) Appl. No.: 10/350,794

(22) Filed: Jan. 24, 2003

(65) Prior Publication Data

US 2003/0181502 A1 Sep. 25, 2003

Related U.S. Application Data

(60) Provisional application No. 60/351,788, filed on Jan. 25, 2002.

(51) Int. Cl.[7] .................. A61K 31/416; C07D 231/56
(52) U.S. Cl. ................ 514/406; 548/356.1; 548/361.1; 548/362.5; 546/275.4; 546/275.7
(58) Field of Search .................. 548/356.1, 361.1, 548/362.5; 514/406; 546/275.4, 275.7

(56) References Cited

FOREIGN PATENT DOCUMENTS

| DE | 197 44 027 A1 | 4/1999 | ......... C07D/471/04 |
|---|---|---|---|
| EP | 0 667 345 A1 | 8/1995 | ......... C07D/405/04 |
| EP | 0 908 456 A1 | 4/1999 | ......... C07D/405/04 |
| JP | 01 190681 | 7/1989 | ......... C07D/471/04 |
| WO | WO 98/16223 | 4/1998 | |
| WO | WO 98/16507 | 4/1998 | |
| WO | WO 01/57024 | 8/2001 | |
| WO | WO 01/87846 | 11/2001 | ......... C07D/231/00 |

OTHER PUBLICATIONS

Ferero et al., "Prolonged Exposure to YC–1 Induces Apoptosis in Adrenomedullary Endothelial and Chromaffin Cells Through a cGMP–independent Mechanism", Neuropharmacology 41:895–906, 2001, XP–002239594.

Flamigni et al., "Control of Survival of Proliferating L1210 Cells by Soluble Guanylate Cyclase and p44/42 Mitogen–activated Protein Kinase Modulators", Biochemical Pharmacology 62:319–328, 2001, XP–002239596.

Lee et al., "Synthesis of 1–Benzyl–3–(5'–hydroxymethyl–2'–furyl)Indazole Analogues as Novel Antiplatelet Agents", J. Med. Chem. 44:3746–3749, 2001, XP–002239593.

Lien et al., "1–Benzyl–3–(5'–hydroxymethyl–2'–furyl)–Indazole (YC–1) Derivatives as Novel Inhibitors Against Sodium Nitroprusside–Induced Apoptosis", J. Med. Chem. 45:4947–4949, 2002, XP–002239595.

Primary Examiner—Golam M M Shameem
(74) Attorney, Agent, or Firm—Fish & Richardson P.C.

(57) ABSTRACT

The present invention features a method for treating sepsis. The method includes administrating to a subject in need thereof an effective amount of a fused pyrazolyl compound of formula (I):

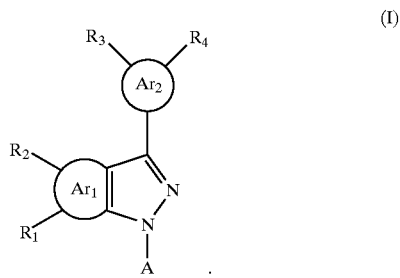

A is H, $C_1 \sim C_6$ alkyl, or

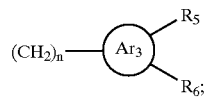

in which n is 0, 1, 2, or 3; each of $Ar_1$, $Ar_2$, and $Ar_3$, independently, is phenyl, pyridinyl, thienyl, furyl, or pyrrolyl; and each of $R_1$, $R_2$, $R_3$, $R_4$, $R_5$, and $R_6$, independently, is XYZ; or $R_1$ and $R_2$ together, $R_3$ and $R_4$ together, or $R_5$ and $R_6$ together are $O(CH_2)_{1-6}O$; in which X is a bond or $C_1 \sim C_6$ alkylene, Y is a bond, O, S, OC(O), OC(O)$(CH_2)_{1-6}$C(O)O, C(O)O, C(O)S, C(O)NH, C(O)N$C_1 \sim C_6$ alkyl, NH, or N$C_1 \sim C_6$ alkyl, and Z is H, halogen, CN, $NO_2$, or $C_1 \sim C_6$ alkyl; and provided that one of $R_3$ and $R_4$ is not H.

25 Claims, 1 Drawing Sheet

METHODS OF TREATING SEPSIS

RELATED APPLICATIONS

This application claims priority to U.S. provisional application No. 60/351,788, filed on Jan. 25, 2002, the contents of which are incorporated herein by reference.

BACKGROUND

Sepsis ranges from systemic inflammatory response to organ dysfunction to multiple organ failure, and ultimately death. See, e.g., Stone (1994) *Science* 264: 365–367; Stone (1994) *Science* 264: 365–367; Karima et al. (1999) *Mol. Med. Today* 5: 123–132; and Parrillo et al. (1990) *Ann Int Med.* 113: 227–242). To prevent sepsis, studies have been conducted on compounds including antioxidants, anti-inflammation agents, and inhibitors of lipopolysaccharide (LPS)-induced nitric oxide (NO) synthesis. See, e.g., Ortolani et al. (2000) *Am J Respir Crit Care Med.* 161: 1907–1911; Kox et al. (2000) *Intensive Care Med.* 26: S124–128; and Boyle et al. (2000) *Circ Res* 87: E18–24). The results of these studies are not satisfactory (Glauser (2000) *Crit Care Med.* 28: S4–8).

Some data indicated that large quantities of NO contribute to the pathogenesis of vascular failure in sepsis (Rees (1995) *Biochem Soc Trans.* 23: 1025–1029). In vivo, large quantities of NO result from: (i) exaggerated synthesis of NO in endothelium after severe attacks such as sepsis, see, e.g., Ochoa et al. (1991) *Ann Surg* 214: 621–626; Nakatsu & Diamond (1989) *Can J Physiol Pharmacol.* 67: 251–262; and Guh et al. (1998) *Mol. Pharmacol.* 53: 467–474; and (ii) up-regulation of the inducible NO synthase (iNOS) as cells respond to bacterial products (e.g., LPS) or inflammatory cytokines (e.g., interleukin-1β and tumor necrosis factor-α), see, e.g., Curran et al. (1989) *J Exp Med.* 170: 1769–1774; and Nakayama et al. (1992) *Am J Respir Cell Mol Biol.* 7: 471–476. NO can react with a superoxide to produce peroxynitrite, which accounts for oxidative injury (Szabo (1996) *Shock.* 6: 79–88). Peroxynitrite has also been reported to be involved in vascular cell apoptosis (Cuzzocrea et al. (1998) *Br J Pharmacol.* 123: 525–537).

Compounds that inhibit vascular cell apoptosis, and therefore prevent vascular and multiple organ failure, are drug candidates for treating or preventing sepsis or symptoms associated with sepsis.

SUMMARY

In one aspect, this invention features a method for treating sepsis. The method includes administrating to a subject (e.g., a mammal, a human, or an animal) in need thereof an effective amount of a fused pyrazolyl compound of formula (I):

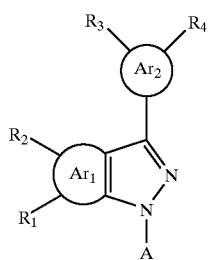

A is H, $C_1$~$C_6$ alkyl, or

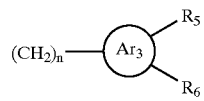

(referred to as "$(CH_2)_nAr_3(R_5)(R_6)$" hereinafter), in which n is 0, 1, 2, or 3; each of $Ar_1$, $Ar_2$, and $Ar_3$, independently, is phenyl, pyridinyl, thienyl, furyl, or pyrrolyl; each of $R_1$, $R_2$, $R_3$, $R_4$, $R_5$, and $R_6$, independently, is XYZ; or $R_1$ and $R_2$ together, $R_3$ and $R_4$ together, or $R_5$ and $R_6$ together are $O(CH_2)_{1-6}O$; in which X is a bond or $C_1$~$C_6$ alkylene, Y is a bond, O, S, OC(O), OC(O)$(CH_2)_{1-6}$C(O)O, C(O)O, C(O)S, C(O)NH, C(O)N$C_1$~$C_6$ alkyl, NH, or N$C_1$~$C_6$ alkyl, and Z is H, halogen, CN, $NO_2$, or $C_1$~$C_6$ alkyl; provided that at least one of $R_3$ and $R_4$ is not H. $(CH_2)_{1-6}$ can be branched or linear. Note that the left atom shown in any substituted group described above is closest to the fused pyrazolyl ring. Also note that when there are one or more R moieties, the R moieties can be the same or different.

Referring to formula (I), a subset of the fused pyrazolyl compounds are those in which A is H, $Ar_1$ is phenyl, $Ar_2$ is phenyl or furyl, and each of $R_1$ and $R_2$ is H.

Another subset of the fused pyrazolyl compounds are those in which A is $(CH_2)_nAr_3(R_5)(R_6)$, $Ar_1$ is phenyl or thienyl, $Ar_2$ is phenyl or furyl, $Ar_3$ is phenyl, and n is 0 or 1. In some embodiments, one of $R_1$, $R_2$, $R_3$, $R_4$, $R_5$, and $R_6$ is COOH, COO—$C_1$~$C_6$ alkyl, $CH_2OH$, CN, $NO_2$, or halogen.

The term "Ar," as used herein, refers to both aryl and heteroaryl groups. Aryl is a hydrocarbon ring system having at least one aromatic ring. An example of aryl is phenyl. Heteroaryl is a hydrocarbon ring system having at least one aromatic ring which contains at least one heteroatom such as O, N, or S. Examples of heteroaryl moieties include, but are not limited to, pyridinyl, thienyl, furyl, or pyrrolyl. Thus, "Ar" includes phenyl, pyridinyl, thienyl, furyl, or pyrrolyl, each of which optionally includes one, two, three, or more substituents. In addition to those assigned above to $R_1$, $R_2$, $R_3$, $R_4$, $R_5$, and $R_6$, the substituents can also be amino, hydroxyl, mercapto, $C_2$~$C_6$ alkenyl, $C_2$~$C_6$ alkynyl, $C_1$~$C_6$ alkoxy, aryl, heteroaryl, cyclyl, or heterocyclyl, wherein alkyl, alkenyl, alkynyl, alkoxy, aryl, heteroaryl, cyclyl, and heterocyclyl are optionally substituted with $C_1$~$C_6$ alkyl, halogen, amino, hydroxyl, mercapto, cyano, or nitro.

As used herein, the term "alkyl" (monovalent) or "alkylene" (divalent) includes both linear and branched alkyl, which optionally includes one or more just-described substituted moieties. The term "aryl" refers to a hydrocarbon ring system (mono-cyclic or bi-cyclic) having at least one aromatic ring. Examples of aryl moieties include, but are not limited to, phenyl, naphthyl, and pyrenyl. The term "heteroaryl" refers to a hydrocarbon ring system (mono-cyclic or bi-cyclic) having at least one aromatic ring which contains at least one heteroatom such as O, N, or S as part of the ring system. Examples of heteroaryl moieties include, but are not limited to, furyl, pyrrolyl, thienyl, oxazolyl, imidazolyl, thiazolyl, pyridinyl, pyrimidinyl, quinazolinyl, and indolyl. The terms "cyclyl" and "heterocyclyl" refer to a partially or fully saturated mono-cyclic or bi-cyclic ring system having from 4 to 14 ring atoms. A heterocyclyl ring contains one or more heteroatoms (e.g., O, N, or S) as part of the ring system. Exemplary cyclyl and heterocyclyl rings are cycylohexane, piperidine, piperazine, morpholine, thiomorpholine, and 1,4-oxazepane.

Set forth below are some specific examples of the fused pyrazolyl compounds which can be used to practice the method of this invention:

Compound 1
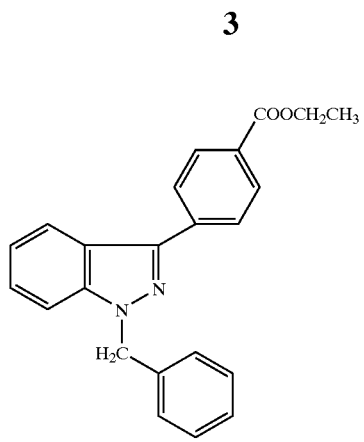
Compound 2
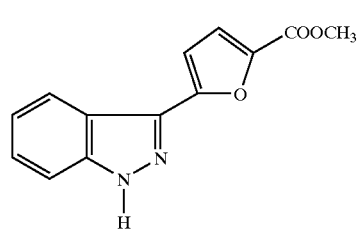
Compound 3
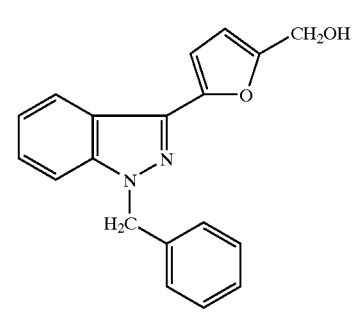
Compound 4
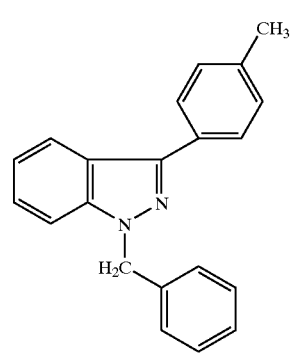
Compound 5
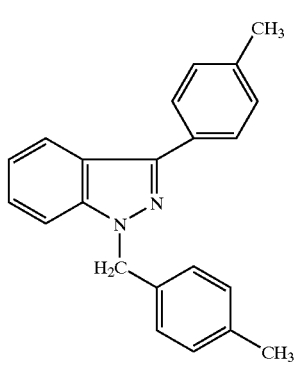
Compound 6
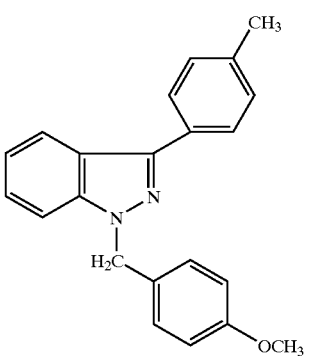
Compound 7
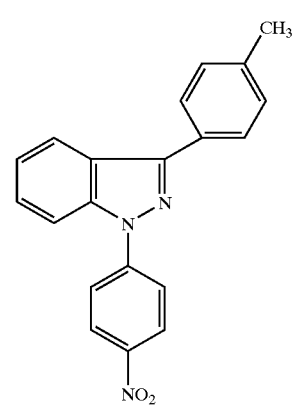
Compound 8
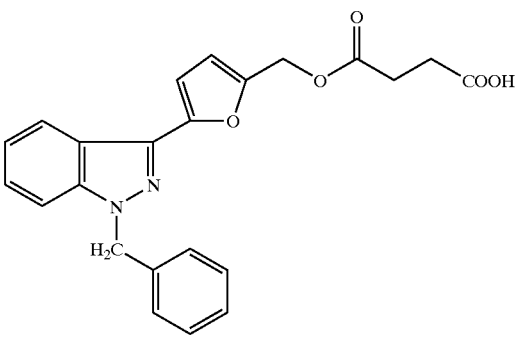
Compound 9
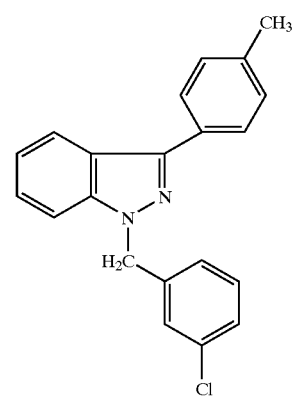

Compound 10
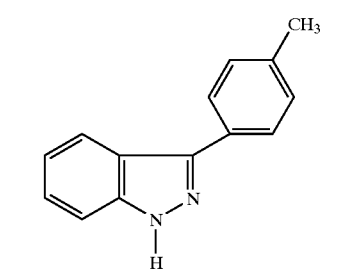
Compound 11
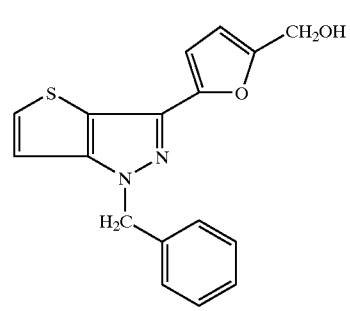
Compound 12
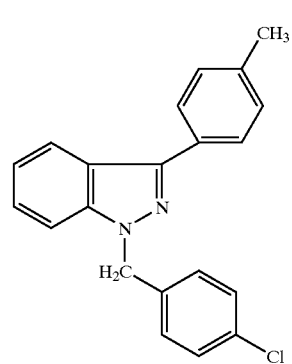
Compound 13
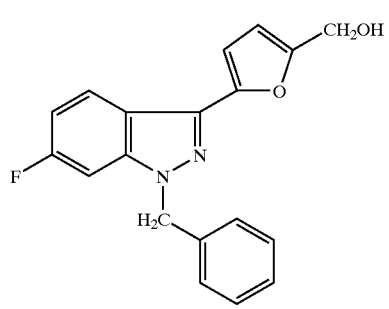
Compound 14
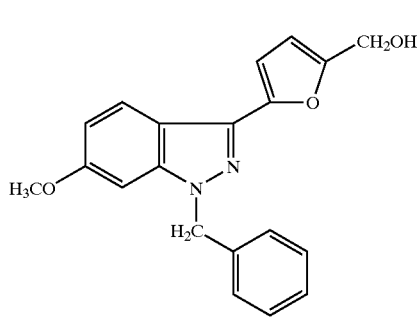
Compound 15
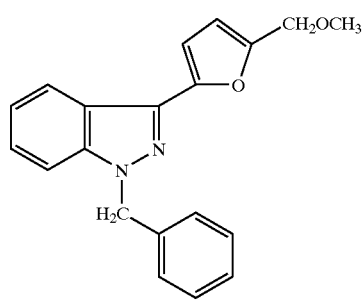
Compound 16
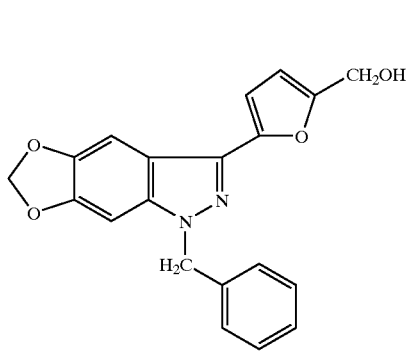
Compound 17
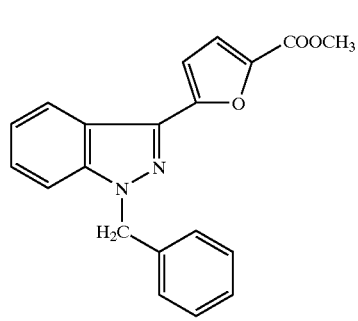
Compound 18
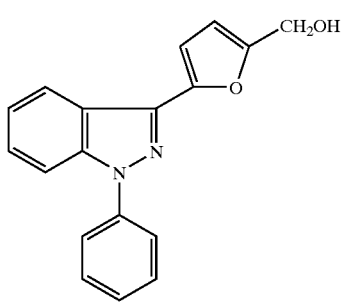
Compound 19
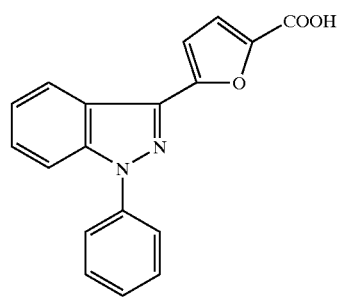

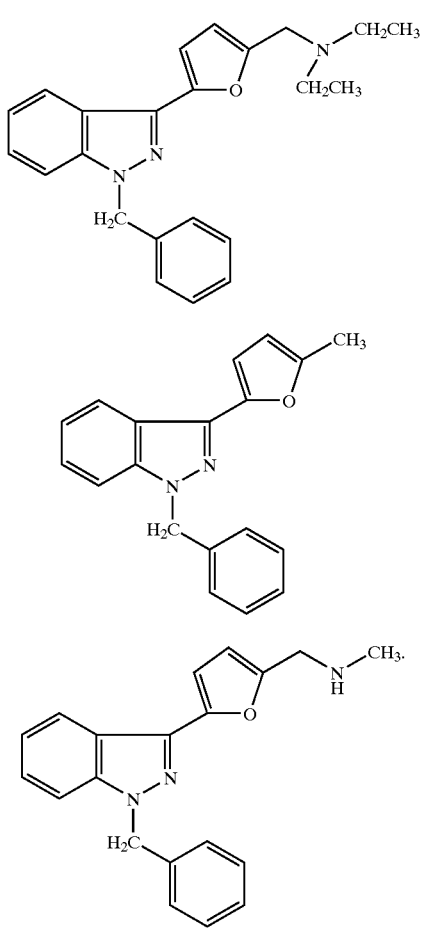

Compound 20

Compound 21

Compound 22

In another aspect, this invention features a compound of formula (I), in which A is H, $C_1$~$C_6$ alkyl, or $(CH_2)_n Ar_3 (R_5)(R_6)$, in which n is 0, 1, 2, 3, or 4; each of $Ar_1$, $Ar_2$, and $Ar_3$, independently, is phenyl, pyridinyl, thienyl, furyl, or pyrrolyl; each of $R_1$, $R_2$, $R_3$, $R_4$, $R_5$, and $R_6$, independently, is XYZ; in which X is a bond or $C_1$~$C_6$ alkylene, Y is a bond, O, S, OC(O), OC(O)($CH_2$)$_{1-6}$C(O)O, C(O)O, C(O)S, C(O)NH, C(O)N$C_1$~$C_6$ alkyl, NH, or N$C_1$~$C_6$ alkyl, and Z is H, halogen, CN, $NO_2$, or $C_1$~$C_6$ alkyl; provided that optionally, $R_1$ and $R_2$ together, or $R_5$ and $R_6$ together are O($CH_2$)$_{1-6}$O; and further provided that X must be $C_1$~$C_6$ alkylene, Y must be OC(O)($CH_2$)$_{1-6}$C(O)O, and Z must be H or $C_1$~$C_6$ alkyl in one of $R_3$ and $R_4$. ($CH_2$)$_{1-6}$ can be branched or linear.

A subset of the just-described fused pyrazolyl compounds of this invention are those in which A is $(CH_2)_n Ar_3(R_5)(R_6)$, $Ar_1$ is phenyl, $Ar_2$ is furyl, $Ar_3$ is phenyl, n is 0 or 1, each of $R_1$, $R_2$, $R_5$, and $R_6$ is H, and one of $R_3$ and $R_4$ is H. An exemplary compound of this invention is Compound 9.

The fused pyrazolyl compounds described above include the compounds themselves, as well as their salts and their prodrugs, if applicable. Such salts, for example, can be formed between a negatively charged substituent (e.g., carboxylate) on a fused pyrazolyl compound and a cation. Suitable cations include, but are not limited to, sodium ion, potassium ion, magnesium ion, calcium ion, and an ammonium cation such as teteramethylammonium ion. Likewise, a positively charged substituent (e.g., amino) can form a salt with a negatively charged counterion. Suitable counterions include, but are not limited to, chloride, bromide, iodide, sulfate, nitrate, phosphate, or acetate. Examples of prodrugs include esters and other pharmaceutically acceptable derivatives, which, upon administration to a subject, are capable of providing the fused pyrazolyl compounds described above (see Goodman and Gilman's, The Pharmacological basis of Therapeutics, $8^{th}$ ed., McGraw-Hill, Int. Ed. 1992, "Biotransformation of Drugs").

In addition, some of the fused pyrazolyl compounds delineated herein have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms.

Further, the aforementioned fused pyrazolyl compounds also include their N-oxides. The term "N-oxides" refers to one or more nitrogen atoms, when present in a fused pyrazolyl compound, are in N-oxide form, i.e., N→O.

Combinations of substituents and variables envisioned by this invention are only those that result in the formation of stable fused pyrazolyl compounds. The term "stable", as used herein, refers to compounds which possess stability sufficient to allow manufacture and which maintains the integrity of the compound for a sufficient period of time to be useful for the purposes detailed herein (e.g., treating sepsis).

In further another aspect, this invention features a method for inhibiting vascular cell apoptosis. The method includes administrating to a subject (e.g., a mammal, a human, or an animal) in need thereof an effective amount of one or more fused pyrazolyl compounds described above.

Also within the scope of this invention is the use of the above-described compounds for the manufacture of a medicament for treating sepsis.

Other features, objects, and advantages of the invention will be apparent from the description and drawings, and from the claims.

DETAILED DESCRIPTION

Figure 1:
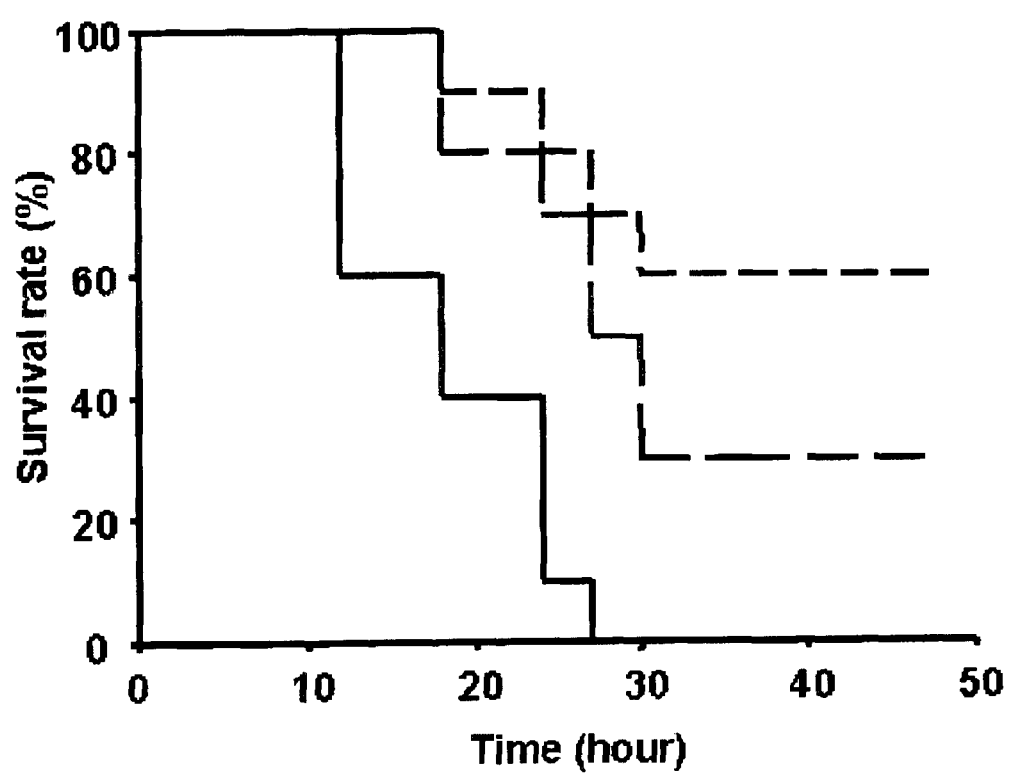
FIG. 1 shows effect of Compound 3 administration on survival of mice suffering form LPS-induced sepsis (solid line: vehicle; long-dashed line: administration two hours after LPS injection; and short-dashed line: administration six hours after LPS injection).

A fused pyrazolyl compound described in the "Summary" section can be prepared by procedures well known to a skilled person in the art (see, e.g., U.S. Pat. No. 5,574,168). They include the following synthetic route: An aryl aryl ketone is first prepared by coupling an arylcarbonyl chloride with another aryl compound. Either aryl compound is optionally mono- or multi-substituted. The ketone then reacts with an arylalkylhydrazine (or an alkylhydrazine, hydrazine), the aryl group of which is also optionally mono- or multi-substituted, to form a hydrazone containing three (or two) aryl groups. The hydrazone group is transformed into a fused pyrazolyl core via an alkylene linker, another aryl group is fused at 4-C and 5-C of the pyrazolyl core, and the third aryl group is directly connected to 3-C of the pyrazolyl core. Derivatives of the fused pyrazolyl compound may be obtained by modifying the substituents on any of the aryl groups.

The chemicals used in the above-described synthetic routes may include, for example, solvents, reagents, catalysts, and protecting group and deprotecting group reagents. The methods described above may also additionally include steps, either before or after the steps described specifically herein, to add or remove suitable protecting groups in order to ultimately allow synthesis of the fused pyrazolyl compounds. In addition, various synthetic steps may be performed in an alternate sequence or order to give the desired compounds. Synthetic chemistry transformations and protecting group methodologies (protection and deprotection) useful in synthesizing applicable fused pyrazolyl compounds are known in the art and include, for example, those described in R. Larock, (*Comprehensive Organic Transformations*, VCH Publishers (1989); T. W. Greene and P. G. M. Wuts, *Protective Groups in Organic Synthesis*, 3$^{rd}$ Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

A fused pyrazolyl compound thus synthesized can be further purified by flash column chromatography, high performance liquid chromatography, or crystallization.

One aspect of this invention is a method for treating sepsis. The method includes administering to a subject in need thereof an effective amount of one or more fused pyrazolyl compounds described above and a pharmaceutically acceptable carrier. The term "treating" refers to using a fused pyrazolyl compound to a subject with the purpose to cure, heal, alleviate, relieve, alter, remedy, ameliorate, improve, or affect sepsis, the symptoms of sepsis or the predisposition toward sepsis. "An effective amount" is defined as the amount of a fused pyrazolyl compound which, upon administration to a subject in need thereof, is required to confer therapeutic effect on the subject. An effective amount of the fused pyrazolyl compound may range from about 0.1 mg/Kg to about 100 mg/Kg. Effective doses will also vary, as recognized by those skilled in the art, depending on route of administration, excipient usage, and the possibility of co-usage with other agents for treating sepsis.

To practice the method of the present invention, a fused pyrazolyl compound can be administered orally, parenterally, by inhalation spray or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A composition for oral administration can be any orally acceptable dosage form including, but not limited to, tablets, capsules, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A sterile injectable composition (e.g., aqueous or oleaginous suspension) can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or di-glycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents.

An inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art.

A carrier in a pharmaceutical composition must be "acceptable" in the sense of being compatible with the active ingredient of the formulation (and preferably, capable of stabilizing it) and not deleterious to the subject to be treated. For example, solubilizing agents, such as cyclodextrins (which form specific, more soluble complexes with fused pyrazolyl compounds), can be utilized as pharmaceutical excipients for delivery of fused pyrazolyl compounds. Examples of other carriers include colloidal silicon dioxide, magnesium stearate, cellulose, sodium lauryl sulfate, and D&C Yellow # 10.

A suitable in vitro assay can be used to preliminarily evaluate the efficacy of a fused pyrazolyl compound in inhibiting vascular cell apoptosis. In vivo screening can also be performed by following procedures well known in the art. See the specific examples below.

Without further elaboration, it is believed that the above description has adequately enabled the present invention. The following specific embodiments are, therefore, to be construed as merely illustrative, and not limitative of the remainder of the disclosure in any way whatsoever. All of the publications, including patents, cited herein are hereby incorporated by reference in their entirety.

Methods

Cell Culture Rat aortic smooth muscle cells (RASMCs) were prepared from Sprague-Dawley rats and cultured in Dulbecco's modified Eagle's medium (DMEM) supplemented with 10% FBS, 100 units/mL penicillin and 100 µg/mL streptomycin (Gibco, Grand Island, N.Y.) as previously described (Yang et al. (2001) Br J Pharmacol. 132: 1531–1541). Cells within six generations were used in the present study. Cells were identified being the smooth muscle cells by immunostaining with monoclonal antibody specific for smooth muscle α-actin.

Cytotoxicity Assay The cytotoxicity assay was carried out using the MTT assay method. MTT (3-(4,5-dimethylthiazol-2-yl)-2,5-diphenyltetrazolium bromide, Sigma Chemical, St. Louis, Mo.) was dissolved in phosphate-buffered saline (PBS) at a concentration of 5 mg/mL and filtered (Millipore, Bedford, Mass.). From this stock solution, 10 µL/100 µL of medium was added to each well of a plate, and the plate was gently shaken and incubated at 37° C. for 2 hours. The treatment of living cells with MTT produced a dark-blue formazan product, whereas no staining was observed in dead cells. After the loading of MTT, the medium was replaced with 100 µL dimethylsulphoxide (DMSO). The extent of reduction of MTT to formazan within cells was quantified by the measurement of $OD_{550}$ with an enzyme-linked immunosorbent assay (ELISA) reader.

In Situ Labeling of Apoptotic Cells In situ detection of apoptotic cells was carried out by using a terminal deoxynucleotidyl transferase (TdT) dUTP nick-end labeling (TUNEL) method with an apoptotic detection kit (Promega, Madison, Wis., USA) as described previously (Guh et al. (1998) *Mol Pharmacol.* 53: 467–474). The TUNEL method identifies apoptotic cells in situ by using TdT to transfer biotin-dUTP to the free 3'-OH of cleaved DNA. The biotin-labeled cleavage sites then were visualized by reaction with fluorescein conjugated avidin (avidin-fluorescein isothiocyanate). Photomicrographs were obtained with a fluorescence microscope (Nikon).

Assay of cGMP Contents At confluence, monolayer cells were incubated with indicated agents for 10 minutes. Then cells were washed twice with ice-cold PBS and lysed with 0.5 mL NaOH (0.1 mol/L). 0.5 mL HCl (0.1 mol/L) was then added to neutralize the assay solution. After the centrifugation (3,000×g for 3 minutes), the supernatant was used for the detection of cGMP content by using a cGMP ELISA kit.

Determination of Caspase-3 Activity

The Caspase-3 activity was assayed with the Caspase-3 colorimetric assay kit (R&D Systems, Inc., Minneapolis, Minn.). After the treatment of cells with indicated agents for ten hours, cells were washed twice with ice-cold PBS, trypsinized, and centrifuged (800×g for 5 minutes), and the cell pellet was re-suspended in pre-cooled lysis buffer obtained from the Caspase-3 colorimetric assay kit. After 10 minutes of incubation on ice, cell homogenates were centrifuged at 10,000×g for 1 minute and supernatants were removed for the determination of caspase-3 activity. Proteolytic reactions were performed in a total volume of 100 µL reaction buffer containing 50 µL of cytosolic extracts and 5 µL DEVD-pNA obtained from the kit. The reaction mixture was incubated at 37° C. for one to two hours and the formation of p-nitroaniline was then measured at 405 nm by an ELISA reader.

Detection of Cytochrome c Release Reaction Cells were trypsinized and centrifuged at 800×g for 10 minutes. Then, the cell pellet was re-suspended in 50 µL of extraction buffer containing 20 mmol/L HEPES, pH 7.5, 10 mmol/L KCl, 1.5 mmol/L $MgCl_2$, 1 mmol/L EDTA, 1 mmol/L EGTA, 1 mmol/L dithithretol, 1 mmol/L PMSF) and incubated for 3 minutes on ice. Cells were managed with 30 strokes and centrifuged at 15,000×g for 15 minutes at 4° C. Aliquots of 20 µg protein were resolved on 15% SDS-polyacrylamide gel and then blotted to PVDF membranes. Membranes were incubated with anti-cytochrome c monoclonal antibody. Then, membranes were incubated with anti-mouse IgG and the expression of cytochrome c was detected as described previously.

Western Blot Analysis After the exposure of cells to the indicated agents for four (for Bcl-2) or six (for cytochrome c) hours, cells were washed twice with ice-cold PBS and reaction was terminated by the addition of 100 µL ice-cold lysis buffer (10 mmol/L Tris-HCl, pH 7.4, 150 mmol/L NaCl, 1 mmol/L EGTA, 0.5 mmol/L phenylmethylsulfonyl fluoride (PMSF), 10 µg/mL aprotinin, 10 µg/mL leupeptin, and 1% Triton X-100). For the detection of phosphorylated Akt, 1 mmol/L $Na_3VO_4$, 1 mmol/L NaF, 50 mmol/L tetrasodium pyrophosphate, 10 nmol/L okadaic acid, 0.25% sodium deoxycholate were included in the lysis buffer. Protein content was determined by the Bio-Rad protein assay (Bio-Rad Laboratories, CA, USA). For Western blot analysis, cell lysates (25 µg/lane) were electrophoresized on 10–15% SDS-polyacrylamide gels, and transferred to a nitrocellulose membrane. The membranes were probed with anti-Bcl-2 or anti-α-tubulin monoclonal antibody, or anti-phosphorylated Akt polyclonal antibody. The transferred membranes were developed with a secondary anti-mouse or anti-rabbit antibody as we previously described (Guh et al. (1998) *Eur. J. Pharmacol.* 359: 281–284). Detection of signal was performed with an enhanced chemiluminescence detection kit (ECL; Amersham International, Little Chalfont, U.K.).

Induction of Endotoxic Shock and Histological Examination In these experiments, mice (25–30 g, ICR strain) were injected intraperitoneally with 60 mg/kg of LPS (dissolved in PBS), and Compound 3 (suspended in carboxymethyl cellulose) was orally administered after the injection of LPS for 2 and 6 hours. The survival rate was monitored every 3 to 6 hours after LPS injection. For histological examination, the lung tissues were put into the 4% paraformaldehyde and embedded in paraffin. The embedded tissues were sectioned at 6-µm thick, stained with hematoxylin-eosin, and analyzed using a microscopy.

Statistical Analysis Data are presented as the mean±SEM for the indicated number of separate experiments. Statistical analysis of data was performed with one-way analysis of variance (ANOVA) followed by a t-test and P-values less than 0.05 were considered significant.

Results

In Vitro Assays

At first, the effect of Compound 3 on sodium nitroprusside (SNP)-induced apoptosis in cultured RASMCs was examined. The data showed that SNP (1 mmol/L) induced a profound cell apoptosis, determined by the MTT assay method and the TUNEL-reaction technique. However, Compound 3 (30 µmol/L) completely abolished the SNP-induced apoptosis. Interestingly, ODQ, an inhibitor of soluble guanylyl cyclase, had no influence on SNP-induced apoptosis, but significantly reversed Compound 3-mediated anti-apoptotic reaction (see Table 1) revealing that the activation of soluble guanylyl cyclase involved in Compound 3-mediated anti-apoptosis other than SNP-induced apoptotic reaction.

The intracellular cGMP levels were also assayed in the present study. Compound 3 alone induced a marked increase of cGMP synthesis (4.2±0.8 fmol/well compared with the basal value of 2.3±0.3 fmol/well). Additionally, the combination of SNP and Compound 3 synergistically evoked more than sixty folds of increase of this cyclic nucleotide formation (252.8±81.8 fmol/well). However, ODQ significantly inhibited the effects of Compound 3 alone (~the basal value) and the combination action of SNP and Compound 3 (~21 fmol/well). Furthermore, using MTT assay method, the cell-permeable cGMP analogue dibutyl-cGMP could significantly reverse SNP-induced apoptosis (data not shown). Taken together, these data suggested that SNP induced a cGMP-independent apoptotic reaction, while Compound 3 prevented the SNP action through a cGMP-dependent signaling pathway.

To examine if the PI 3-kinase and mitogen-activated protein kinase (MAPK) were involved in Compound 3-mediated anti-apoptosis, their selective inhibitors were used in the functional determination. The PI 3-kinase inhibitor, wortmannin, and the mitogen-activated protein kinase (MEK) inhibitor, PD98059, significantly reversed the Compound 3 action revealing that the activation of PI 3-kinase might play a central role in Compound 3-induced anti-apoptotic effect.

It is well suggested that the lipid products of PI 3-kinase bind with high affinity and specificity to the Akt/PKB PH domain and then trigger cell survival signaling pathway. In the present study, the phosphorylated Akt expression was examined using Western blotting analysis. The results showed that both Compound 3 alone and its combination with SNP induced the profound increase of phosphorylated Akt expression. These effects were profoundly inhibited by ODQ and wortmannin suggesting that the activation of PI 3-kinase induced by Compound 3 is a downstream event of cGMP synthesis.

The effects of SNP and Compound 3 on Bcl-2 levels and cytochrome c release reaction were studied. SNP (1 mmol/L) exposure caused a profound down-regulation of Bcl-2 expression and cytochrome c release into cytosol. The action of SNP was completely prevented by the treatment of cells with Compound 3. However, ODQ and wortmannin fully reversed the preventive action to Compound 3. These data suggest that the cGMP-dependent PI 3-kinase-involved signaling pathway to Compound 3 action is contributed to the prevention of Bcl-2 down-regulation and cytochrome c release caused by SNP.

The caspase-3 activity was determined after the exposure of cells to SNP (1 mmol/L). The results showed that SNP significantly increased the caspase-3 activity in RASMCs; however, Compound 3 completely inhibited this enzyme activity to SNP action. Moreover, Compound 3-mediated inhibitory effect was also partially but significantly reversed by ODQ and wortmannin, respectively. When the apoptosis percentage and caspase-3 activity were further analyzed for any correlation, a positive linear regression was obtained with a correlation coefficient ($r^2$ value) of 0.980 suggesting the crucial role of the regulation of caspase-3 activity in SNP-induced effect and the anti-apoptotic action of Compound 3.

The effects of Compounds 1–22 on sodium nitroprusside (SNP)-induced apoptosis in cultured VSMCs were examined. 16 compounds showed inhibitory effect on SNP (1 mmol/L) induced apoptosis. Some of them completely abolished the SNP-induced apoptosis.

In Vitro Assays

To investigate the therapeutic potential of Compound 3 in septic treatment, the LPS-induced septic death in mouse model was used. The intraperitoneal administration of LPS (60 mg/kg) caused a cumulative animal death within 10 to 28 hours. However, the oral treatment of Compound 3 (10 mg/kg) after two hours of LPS application (i.e., post-treatment of Compound 3) significantly increased the survival rate of mice (FIG. 1). Moreover, these survived mice remained vigorous more than one month after the LPS initiation.

The histological examination of the in vivo animal study was also observed. The control mouse showed an intact histological appearance of lung tissues. After the LPS application for 28 hours, the animal exhibited the damaged blood vessels and a massive leakage of blood cells out of the circulation in the lung tissues. However, the healthy mouse of post-treated Compound 3 group showed the intact blood vessels without the infiltration of blood cells.

The effect of vascular smooth muscle cell (VSMC) apoptosis is obviously environment-dependent. VSMC apoptosis has been studied well in atherosclerosis and neointimal formation post injury (Mallat et al. (1997) *Circulation* 96: 424–428; and Newby & George (1996) *Curr Opin Cardiol.* 11: 574–582.); however, there is less attention focus on its association with sepsis. The actions of NO on apoptosis are dependent on cell types, cell concentrations, radical circumstances, and also the redox state of cells (Yabuki et al. (1997) *Free Radical Res.* 27: 325–335; and Filippov et al. (1997) *J Clin Invest.* 100: 942–948). Compound 3 prevented SNP-induced apoptotic effect in a cGMP-dependent manner based on the observations that Compound 3 in the combination with SNP synergistically increased cGMP synthesis, dibutyl-cGMP efficiently mimicked Compound 3-mediated effect, and ODQ significantly reversed the Compound 3 action. However, there still remained about 20% of ODQ-irresponsible action in Compound 3-mediated effect.

The mechanisms suggested for NO-induced cytotoxicity include inactivation of the mitochondrial respiratory chain, DNA damage, and Bcl-2 down-regulation/Bax up-regulation (Bolanos et al. (1997) *J Neurochem.* 68: 2227–2240; and Tamatani et al. (1998) *Cell Death Differ.* 5: 911–919). As discussed above, SNP induced a significant down-regulation of Bcl-2 proteins other than the influence on Bax expression (data not shown); it also stimulated the release reaction of cytochrome c into the cytosol and the activation of caspase-3 activity. These data demonstrate the regulation of Bcl-2/cytochrome c/caspase-3 signaling pathways in SNP-mediated apoptotic mechanism in RASMCs. However, Compound 3 almost completely blocked all of these apoptotic events to SNP action. Furthermore, ODQ profoundly reversed the Compound 3-mediated effects revealing that Compound 3 behaved a cGMP-dependent anti-apoptotic action.

It has been suggested that the increase in cyclic nucleotide synthesis and the following activation of PI 3-kinase play a central role on the prevention of apoptotic reaction in several types of cells (Webster & Anwer (1998) *Hepatology.* 27: 1324–1331). Furthermore, it has been reported that in some cell types, such as cytokine-activated mesangial cells, cGMP may regulate the activation of p42/44 MAPK by NO (Callsen et al. (1998) *J Immunol.* 161: 4852–4858). It has been shown above that wortmannin but not PD98059 reversed the Compound 3-mediated effects. Further, the Akt phosphorylation was markedly induced in the presence of Compound 3 and, however, this action was diminished by ODQ. These results suggest that the PI 3-kinase is a downstream effector of sGC activation after Compound 3 application and involves in the anti-apoptotic mechanism. In contrast, p42/44 MAPK pathway is not relevant for Compound 3-mediated survival in RASMCs. Interestingly, although it was not statistically significant, Compound 3 alone induced a modest increase in cell number (11%, Table 1) in RASMCs. Both ODQ and PD98059 completely inhibited this Compound 3-induced cell proliferation implying the involvement of sGC and p42/44 MAPK activities.

This study indicates the anti-apoptotic role of PKC activation. However, the data showed that Ro-318220, a selective PKC inhibitor, had little influence on Compound 3-mediated anti-apoptotic action (107.1±3.1% vs. 100.6±5.5% cell survival of Compound 3 plus SNP group, P=0.32, n=7) suggesting the irrelevance of PKC activity in Compound 3 action.

The effect of Compound 3 on the prevention of LPS-induced septic death in mice has been shown; especially, the post-treatment of Compound 3 was carried out. The data demonstrate a significant decrease of mortality rate in LPS-treated mice. The lung tissues were also examined as it is well suggested that the lung failure is one of the most significant causes in septic death. Based on the histological examination, the results showed that the animal exhibited the damaged blood vessels and a massive leakage of blood cells out of the circulation in the lung tissues after the LPS application. Further, the mice of post-treated Compound 3 group showed the intact blood vessels without the infiltration of blood cells and behave vigorous as usual.

The effects of Compound 3 on the other pharmacological activities were also determined. Previously, Compound 3 had no inhibition on cyclooxygenase activity (Ko et al. (1994) *Blood.* 84: 4226–4233); it also showed little inhibition on LPS/interferon γ-induced tumor necrosis factor-α release in NR8383 macrophages (18.5±1.2 ng/mL as compared with the control of 15.5±1.3 ng/mL, P=0.13, n=4) and the reduction of cytochrome c by superoxide anion generated from the xanthine/xanthine oxidase system (40±0.6% as compared with the control of 42.0±2.1%, P=0.4, n=4). Furthermore, the free radical-scavenging activity of Compound 3 was examined using the stable radical 1,1-diphenyl-2-picrylhydrazyl. Compound 3 exhibited little free radical-scavenging activity (data not shown). In another experiment, after a 24-hour stimulation of murine macrophage RAW 264.7 cells by LPS (1 μg/mL), a profound formation of NO was observed. Nevertheless, Compound 3 failed to affect this LPS-evoked effect in the present study (53.4±12.3 μmol/L nitrite as compared with the control of 68.8±13.4 μmol/L nitrite, P=0.43, n=4). These results indicate that Compound 3 exhibits little activities of anti-inflammation, antioxidant, and anti-LPS action on NO formation and rule out the contribution of these effects on Compound 3-mediated animal survival. Thus, based on the discussions above, Compound 3 has a significant role of the anti-apoptotic effect on septic death in mice.

TABLE 1

Effects of sodium nitroprusside (SNP), Compound 3, and ODQ on the regulation of cell survival in rat aortic smooth muscle cells.

| Treatment | Cell survival (%) | n |
|---|---|---|
| Control | 100 ± 0 | 6 |
| SNP | 49.3 ± 4.4* | 6 |
| Compound 3 | 111.3 ± 8.8 | 6 |
| SNP + Compound 3 | 102.9 ± 8.1[+] | 6 |
| ODQ | 99.5 ± 5.7 | 5 |
| ODQ + Compound 3 | 96.1 ± 4.2 | 7 |
| ODQ + SNP + Compound 3 | 69.6 ± 4.0[#] | 6 |

Data are expressed as mean ± SEM of five to seven experiments, n represents the number of independent experiment.
*$P < 0.001$ compared with the control;
[+]$P < 0.001$ compared with SNP alone;
[#]$P < 0.01$ compared with the SNP plus Compound 3.

Other Embodiments

All of the features disclosed in this specification may be combined in any combination. Each feature disclosed in this specification may be replace by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, a compound structurally analogous to a fused pyrazolyl compound can also be used to practice the present invention. Thus, other embodiments are also within the claims.

What is claimed is:

1. A method for treating sepsis, comprising administrating to a subject in need thereof an effective amount of a compound of formula (I):

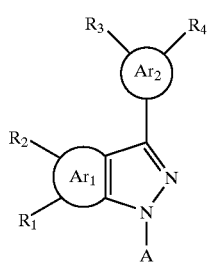

(I)

wherein
A is H, $C_1$~$C_6$ alkyl, or

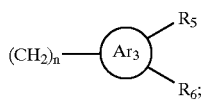

in which n is 0, 1, 2, or 3;
each of $Ar_1$, $Ar_2$, and $Ar_3$, independently, is phenyl, pyridinyl, thienyl, furyl, or pyrrolyl; and
each of $R_1$, $R_2$, $R_3$, $R_4$, $R_5$, and $R_6$, independently, is XYZ; or $R_1$ and $R_2$ together, $R_3$ and $R_4$ together, or $R_5$ and $R_6$ together are $O(CH_2)_{1-6}O$; in which X is a bond or $C_1$~$C_6$ alkylene, Y is a bond, O, S, OC(O), OC(O)$(CH_2)_{1-6}$C(O)O, C(O)O, C(O)S, C(O)NH, C(O)N$C_1$~$C_6$ alkyl, NH, or N$C_1$~$C_6$ alkyl, and Z is H, halogen, CN, $NO_2$, or $C_1$~$C_6$ alkyl; and provided that one of $R_3$ and $R_4$ is not H.

2. The method of claim 1, wherein A is H.
3. The method of claim 2, wherein $Ar_1$ is phenyl.
4. The method of claim 3, wherein $Ar_2$ is phenyl.
5. The method of claim 4, wherein each of $R_1$ and $R_2$ is H.
6. The method of claim 3, wherein $Ar_2$ is furyl.
7. The method of claim 6, wherein each of $R_1$ and $R_2$ is H.
8. The method of claim 1, wherein A is

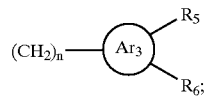

9. The method of claim 8, wherein $Ar_1$ is phenyl.
10. The method of claim 9, wherein $Ar_2$ is phenyl.
11. The method of claim 10, wherein $Ar_3$ is phenyl.
12. The method of claim 11, wherein n is 0 or 1.
13. The method of claim 12, wherein one of $R_1$, $R_2$, $R_3$, $R_4$, $R_5$, and $R_6$ is COOH, COO—$C_1$~$C_6$ alkyl, $CH_2OH$, CN, $NO_2$, or halogen.
14. The method of claim 9, wherein $Ar_2$ is furyl.
15. The method of claim 14, wherein $Ar_3$ is phenyl.
16. The method of claim 15, wherein n is 0 or 1.
17. The method of claim 16, wherein one of $R_1$, $R_2$, $R_3$, $R_4$, $R_5$, and $R_6$ is COOH, COO—$C_1$~$C_6$ alkyl, $CH_2OH$, CN, $NO_2$, or halogen.
18. The method of claim 9, wherein $Ar_3$ is phenyl.
19. The method of claim 9, wherein n is 0 or 1.
20. The method of claim 8, wherein $Ar_1$ is thienyl.
21. The method of claim 20, wherein $Ar_2$ is furyl.
22. The method of claim 21, wherein $Ar_3$ is phenyl.
23. The method of claim 22, wherein n is 0 or 1.
24. The method of claim 23, wherein one of $R_1$, $R_2$, $R_3$, $R_4$, $R_5$, and $R_6$ is COOH, COO—$C_1$~$C_6$ alkyl, $CH_2OH$, CN, $NO_2$, or halogen.
25. The method of claim 1, wherein the compound is

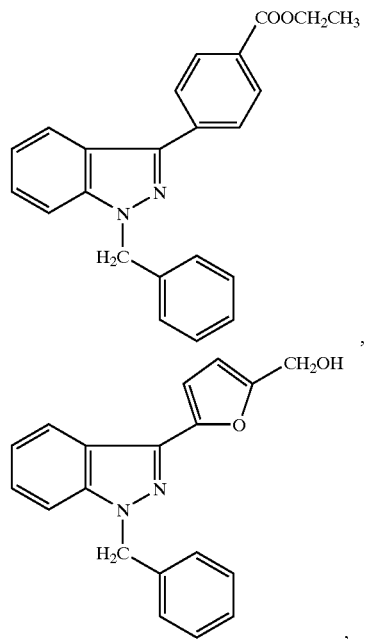

-continued
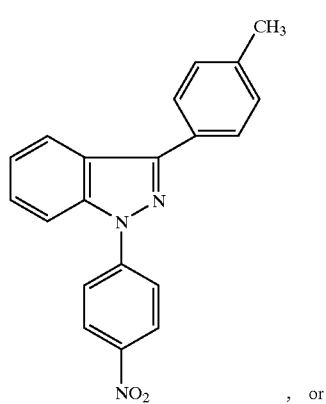
, or
-continued
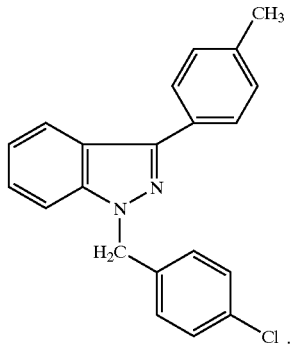
* * * * *